United States Patent
Pabreza et al.

(10) Patent No.: US 9,784,683 B2
(45) Date of Patent: Oct. 10, 2017

(54) SURFACE ENHANCED RAMAN SCATTERING (SERS) SENSOR AND A METHOD FOR PRODUCTION THEREOF

(71) Applicant: ATO ID, UAB, Vilnius (LT)

(72) Inventors: Evaldas Pabreza, Vilnius (LT); Gediminas Raciukaitis, Vilnius (LT)

(73) Assignee: ATO ID, UAB, Vilnius (LT)

(*) Notice: Subject to any disclaimer, the term of this patent is extended or adjusted under 35 U.S.C. 154(b) by 0 days.

(21) Appl. No.: 14/891,285

(22) PCT Filed: Jul. 29, 2013

(86) PCT No.: PCT/IB2013/056192
§ 371 (c)(1),
(2) Date: Nov. 13, 2015

(87) PCT Pub. No.: WO2014/188237
PCT Pub. Date: Nov. 27, 2014

(65) Prior Publication Data
US 2016/0123888 A1    May 5, 2016

(30) Foreign Application Priority Data
May 24, 2013  (LT) .................................. 2013 053

(51) Int. Cl.
*G01N 21/65*  (2006.01)
*C03C 23/00*  (2006.01)
(Continued)

(52) U.S. Cl.
CPC ........... *G01N 21/658* (2013.01); *C03C 17/09* (2013.01); *C03C 23/0025* (2013.01);
(Continued)

(58) Field of Classification Search
CPC ..................................................... G01N 21/658
See application file for complete search history.

(56) References Cited

U.S. PATENT DOCUMENTS

| | | | |
|---|---|---|---|
| 7,586,601 B2 * | 9/2009 | Ebstein | B01L 3/5088 356/244 |
| 7,864,312 B2 | 1/2011 | Mazur et al. | |

(Continued)

OTHER PUBLICATIONS

Shaheen, M. E., J. E. Gagnon, and B. J. Fryer. "Femtosecond laser ablation behavior of gold, crystalline silicon, and fused silica: a comparative study." Laser Physics 24.10 (2014): 106102.*

(Continued)

*Primary Examiner* — Shawn Decenzo
(74) *Attorney, Agent, or Firm* — Bryant J. Keller; Kirton McConkie

(57) ABSTRACT

A plasmonic sensor, having at least a substrate, a laser processed active surface area on the said substrate, and a metal coating on the activate surface, where the laser processed surface is fabricated by means of short laser pulses in such a way that in a shallow layer of the surface material, the viscosity is reduced and under the influence of the same pulse, which was used to reduce the viscosity, or a successive incident one or more pulses a self-organized, stochastic nanostructure is formed, which has features smaller than 1 μm. In some implementations, the substrate material is amorphous, such as soda-lime glass or similar. Also disclosed is a slide and/or a slip cover, which are used in microscopy, for forming the active sensor area on top surface of it.

20 Claims, 4 Drawing Sheets

(51) Int. Cl.
G01N 21/552 (2014.01)
C23C 14/14 (2006.01)
C23C 14/34 (2006.01)
C03C 17/09 (2006.01)
G01N 21/25 (2006.01)

(52) U.S. Cl.
CPC .............. *C23C 14/14* (2013.01); *C23C 14/34* (2013.01); *G01N 21/554* (2013.01); *C03C 2218/31* (2013.01); *G01N 2021/258* (2013.01); *G01N 2021/651* (2013.01)

(56) References Cited

U.S. PATENT DOCUMENTS

2011/0013192 A1* 1/2011 Yang ............... G01N 21/554 356/445
2015/0109619 A1* 4/2015 Sugimoto ........... G01N 21/658 356/445

OTHER PUBLICATIONS

Wang, Cong, et al. "The thresholds of surface nano-/micro-morphology modifications with femtosecond laser pulse irradiations." Nanotechnology 21.7 (2010): 075304.*

Nayak B. K., et al., "Self-organized micro/nano structures in metal surfaces by ultrafast laser irradiation", Optics and Lasers in Engineering, vol. 48, No. 10, Oct. 1, 2010 (Oct. 1, 2010), pp. 940-949, XP055090354, ISSN: 0143-8166, DOI: 10.10161j.optlaseng.2010.04.010, whole document.

Juergen, Reif, et al., "Long-time feedback in self-organized nanostructures formation upon multipulse femtosecond laser ablation", Proceedings of SPIE, vol. 7586, Feb. 11, 2010 (Feb. 11, 2010), pp. 7586OH-7586OH-9, XP055090498, ISSN: 0277-786X, DOI: 10.1117112.846978, whole document.

Lei, Su, et al., "nanostructures fabricated in chalcogenide glass for use as surface-enhanced Raman scattering substrates", Optics Letters, The Optical Society, vol. 34, No. 11, Jun. 1, 2009 (Jun. 1, 2009), pp. 1645-1647, XP001524476, ISSN: 0146-9592, whole document.

* cited by examiner

SURFACE ENHANCED RAMAN SCATTERING (SERS) SENSOR AND A METHOD FOR PRODUCTION THEREOF

TECHNICAL FIELD

The invention relates to the field of molecular diagnostics, and more particular it relates to the structured Surface Enhanced Raman Scattering (SERS) sensors. Such detectors are used for the detection of small concentrations of materials in an analyte and the label-free identification of materials.

BACKGROUND ART

Raman scattering is an effect related to the inelastic scattering of photons during their interaction with ions present in a material. Typically, laser radiation of a narrow spectral bandwidth (<1 nm) is used for the stimulation of Raman scattering, and the spectra of the scattered light is measured, whereas the peaks in the spectra are shifted to the red (Stokes shift) or blue (Anti-Stokes shift) side of the spectrum. Under appropriate experimental conditions, according to the positions of the peaks in the spectrum, the materials inside an analyte can be identified.

Surface enhanced Raman scattering (SERS) sensors are usually used to amplify a very weak Raman scattering signal by multitude of times. Such amplification is achieved by the use of plasmonic effects, and especially by the localized surface plasmons. In order to create the right conditions for the interaction between a photon and the surface plasmons, it is necessary to form an array of submicron structures and cover it with a coating of a precious metal, usually gold or silver, as to allow the formation of separate metal islands. The shape, size and position of the structures with respect to each other determine how the plasmons interact with the incident photons of the laser radiation and with those photons, who experienced Raman scattering. The stronger the interaction between plasmons and photons is, the more intense is the amplification of Raman scattering.

SERS sensors can be used in molecular diagnostics and are particularly important for such branches of industry as biotechnologies, drug development, food and soil contamination measurements, forensics, border control, etc.

A plasmon is a quasi-particle described as a quantized oscillation of free electron plasma. A plasmon can couple with a photon forming a new quasiparticle—plasmon polariton. Surface plasmons are surface localized plasmons, which strongly interact with light incident on a surface resulting in a polariton.

In order to create surface plasmons, which interact with the light radiation in the visible spectral range, surface structures, which are the size of tens or hundreds of nanometers, must be formed. The realization of the Surface Enhanced Raman Scattering (SERS) principle requires that the plasmon resonance condition be met.

The most active plasmon resonance phenomena occur on the surface of noble metals, such as gold or silver. Mainly, this is related to the large number of free electrons, present at the metal surface. Due to this reason, in addition to the fact that such metals do not oxidize, they are most often chosen for the production of SERS sensors.

As mentioned previously, the surface structure is particularly important for SERS applications. In case of surface plasmons, the plasmon resonance conditions for small metal elements are strongly dependent on the shape and relative position of those metal particles with respect to each other.

Recently, the influence of the gap between two metal particles on the amplification of the electromagnetic field has become especially frequently emphasized. It has been noticed that this parameter (gap size) has the largest impact on the overall amplification of a SERS. The whole field of research on SERS, where the main goal is to detect single analyte molecules, is most often based on this phenomenon. In presence of an especially small gap, localized surface plasmon modes of both metal particles interact, thus forming hybridized modes.

Detectors having a strong Raman scattering amplification are often fabricated by employing nanotechnology principles. Thus, metal islands of the desired size, with small gaps in-between, are obtained. For this reason this research field is often called nanoplasmonics.

In some cases, for the manufacture of SERS devices, methods of laser processing are employed. They do not require physical contact, no additional chemical treatment is necessary after processing, and also during laser processing little additional operations are required. Surface structure patterns, which comprise repeatable features with a period smaller than one micrometer, are formed by using the laser initiated formation of self-organized nanostructures. Few prior-art patents indicate that surface structure patterns, formed by an ultra-short pulse laser, turn-out to be good substrates for SERS sensors possessing high amplification capabilities. Such sensors are often called plasmonic sensors or substrates.

A U.S. Pat. No. 7,586,601, published on Aug. 9, 2009, describes femtosecond laser nanostructured substrates, which are used for the production of SERS sensors. These substrates are made of a semiconductor or a metal. The surface of the material is processed with ultra-short laser pulses, creating ripples or self-ordered nanostructures, and later a noble metal film (e.g., silver or gold) is deposited onto the resulting nanostructured surfaces.

Another U.S. Pat. No. 7,864,312, published on Apr. 1, 2011, describes a substrate for Raman spectroscopy, having a metal coating. The substrate is processed with short laser pulses in order to generate micron-sized or smaller structures on the surface. The structured surface can then be coated with discontinuous metal coating characterized by one or more metallized surface regions and a plurality of surface gaps.

Both prior-art patents describe the formation of smaller than a micrometer size structures by short or ultra-short laser pulses on a surface of a metal or semiconductor. This process is also known as ripple formation. Ripples described in these patents form when ablation occurs on the surface of the material, that is to say that when a material is evaporated directly from the solid state, omitting the melting phase. Nonetheless ripples can be formed only on the surface of specific materials. Most commonly metals or semiconductors are used. It is popular to use silicon, sapphire, germanium, fused silica or similar. When forming ripples on a semiconductor or other crystalline material (sapphire or fused silica) surface, it is necessary to irradiate the material surface with a few thousands of laser pulses. The more pulses are used, the more apparent the ripple structure becomes, yet this process is time consuming. For example, processing a surface area of 1 mm$^2$ with a fairly fast laser (for example when the pulse repetition rate is 600 kHz) can take tens of minutes. Furthermore, further increase in ripple aspect ratio is usually achieved by using aggressive acids, which require very careful handling. This is not convenient and makes manufacturing costly.

Also, the material, used in earlier solutions, is expensive. This results in a prime cost of a sensor and complicates production operations.

DISCLOSURE OF INVENTION

Technical Problem

Summary

In order to eliminate the drawbacks indicated above, this invention provides a cost effective and rapid method for producing SERS sensors (Raman scattering enhancing substrates). The substrate (1) formed from an amorphous material, preferably soda-lime glass, is processed with an ultra-short pulse laser (4) radiation. In this process, viscosity of the substrate material is decreased instead of ablation, i.e. reduction of viscosity (for simplicity, will be referred to as 'melting of the material') occurs due to the absorption of the laser pulse energy in a shallow layer of the substrate material. Thereafter, the melted material interacts with the incident laser pulses and forms self-organized stochastic nanostructures. In most cases, barely few laser pulses for a single surface point is sufficient for the nanostructures to transform into the necessary pattern, suitable for the formation of the active area of the SERS sensor.

For production of SERS sensors using this method, it is convenient to use microscope slides or cover slips, which are used in microscopy, as substrates for the sensor. Such glass work pieces are usually already well pre-cleaned and packaged, therefore they do not require additional processing before the laser treatment.

Various optical and mechanical systems, which are used together with a short-pulse, preferably from 100 fs to 100 ps, laser, can be used for fabrication. The nanostructures being formed are influenced by both—the wavelength of the short-pulse laser radiation and the environment of the substrate during fabrication. A shorter wavelength and a larger refractive index result in the formation of smaller size nanostructures. The feature size of the nanostructures must be adjusted to the wavelength of the laser used for stimulating Raman scattering—the shorter the wavelength, the finer the structure pattern must be sought. Nonetheless, SERS sensors produced by using the method, described in this patent, have a large variety of feature sizes, and one sensor meets the plasmon resonance conditions for a wide range of excitation wavelengths.

After laser processing the substrates can be washed in acetone or distilled water, preferably in an ultrasound cleaner—removing the debris, which has been formed during processing. The cleaned substrates are coated with a metal coating. Most commonly a coating of gold or silver or platinum or copper is used in the production of SERS sensors. Silver is most preferable for a wide range of excitation wavelengths, but gold or copper are more suited when working with excitation radiation in the infrared range of the spectrum.

BRIEF DESCRIPTION OF DRAWINGS

Description of Drawings

In order to understand the invention better, and appreciate its practical applications, the following pictures are provided and referenced hereafter. Figures are given as examples only and in no way limit the scope of the invention.

Figure 1:
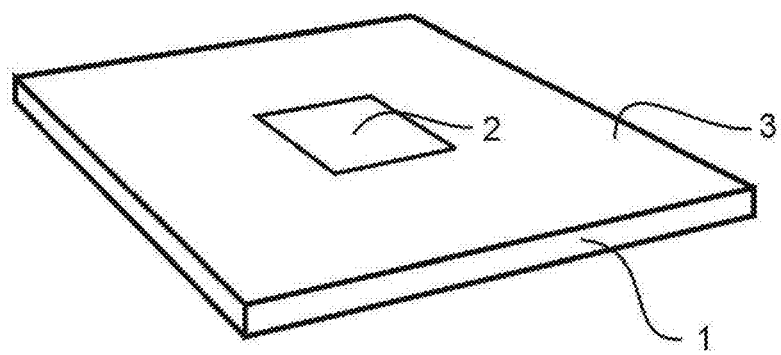
Figure 2:
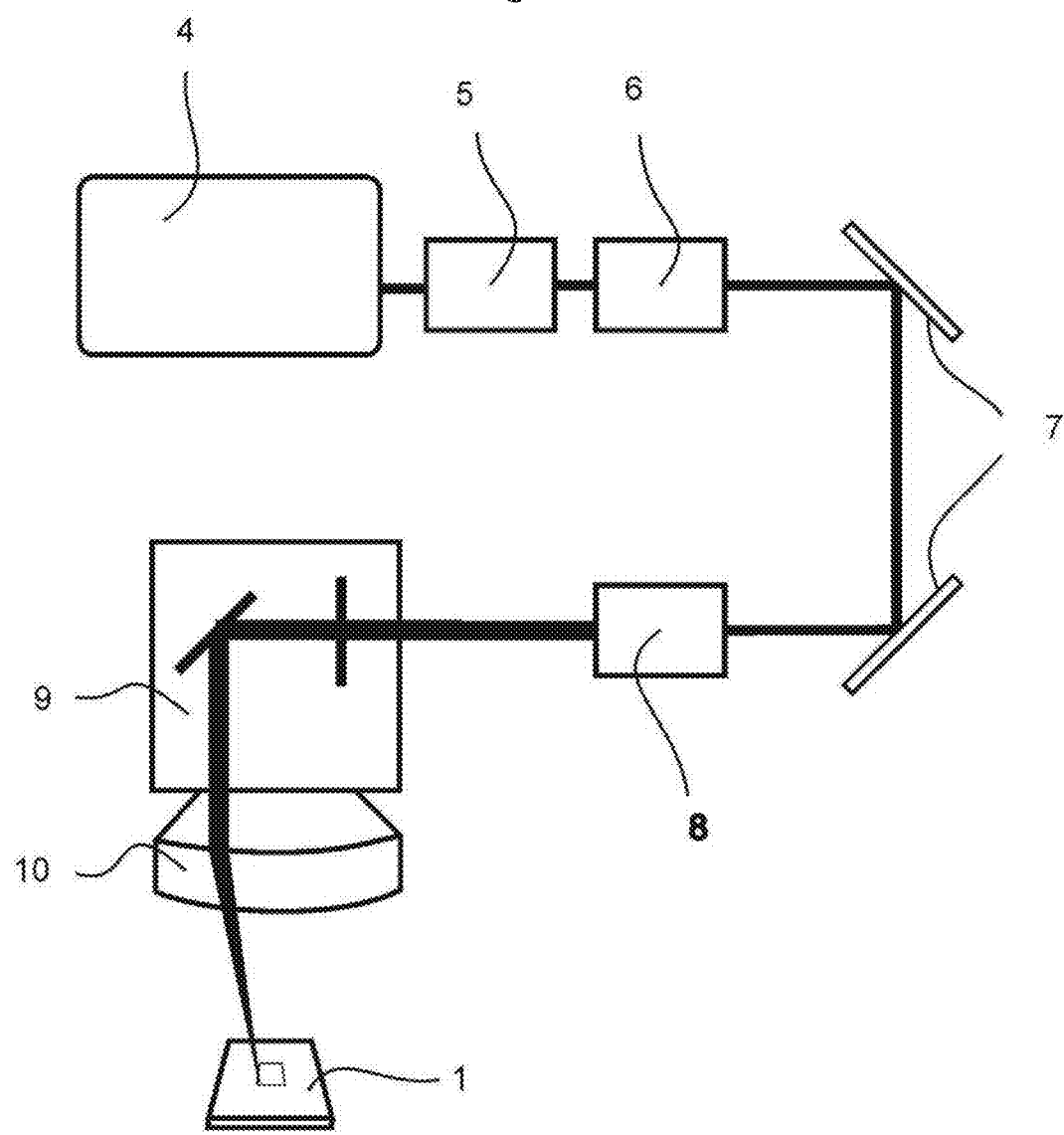
Figure 3:
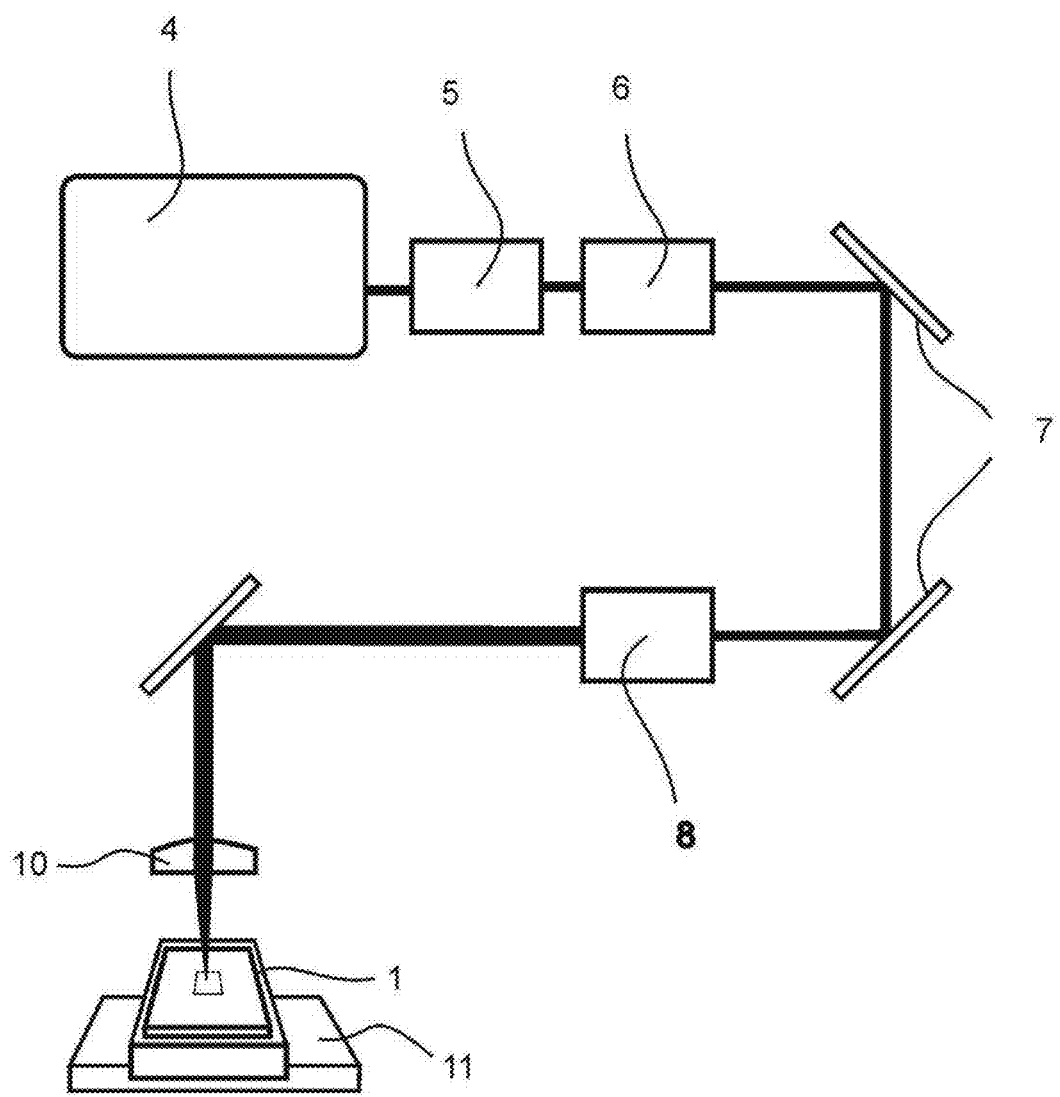
Figure 4:
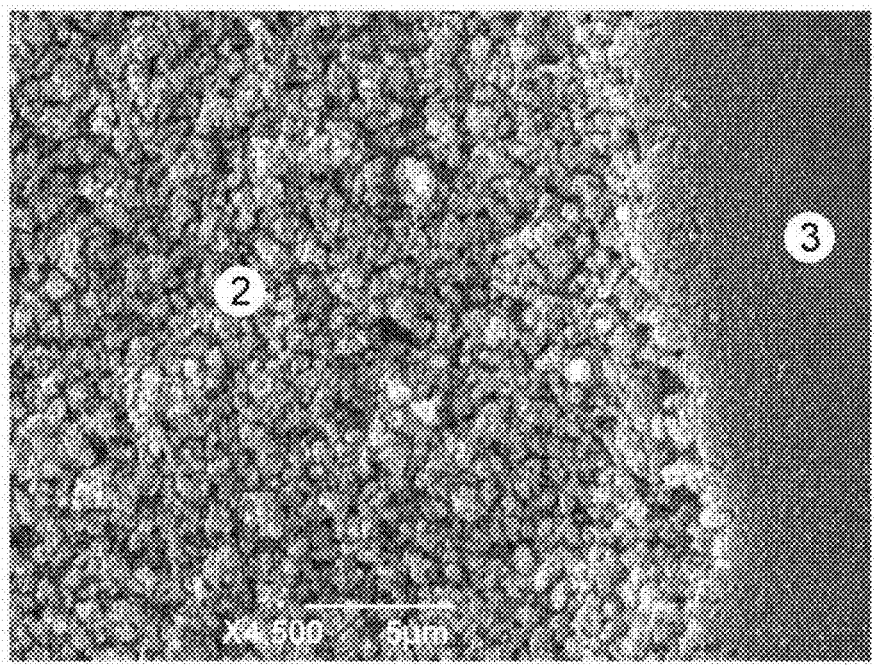
Figure 5:
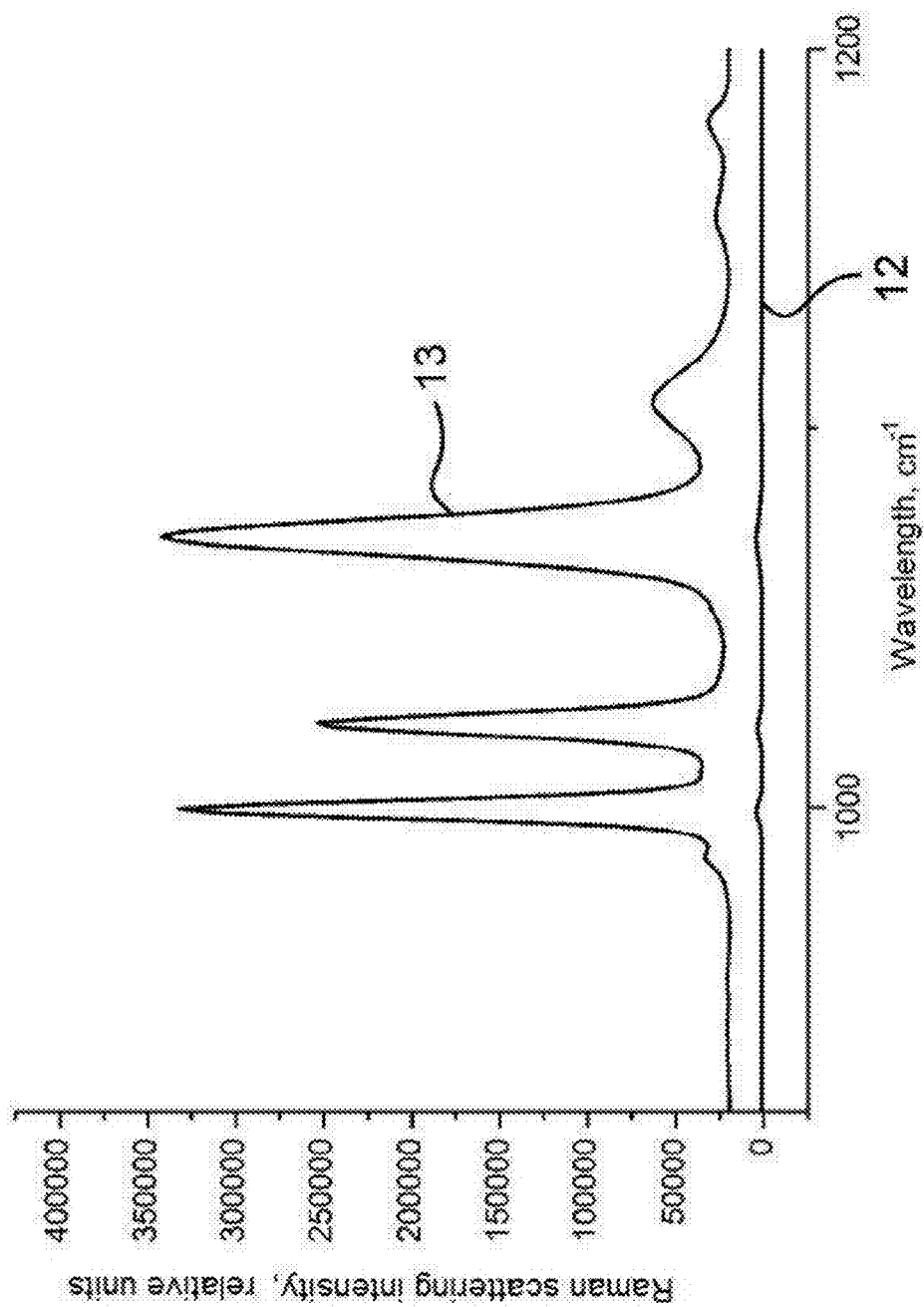

FIG. 1 illustrates the exemplary composition of the SERS sensor;

FIG. 2. illustrates the principle scheme of the SERS sensor fabrication assembly, where the beam is manipulated by means of galvanometric scanners;

FIG. 3. illustrates the principle scheme of the SERS sensor fabrication assembly, where the sample is translated under stationary fixed optics;

FIG. 4. illustrates the magnified laser processed surface area, where stochastic self-organized structures, formed after surface melting and interaction with short laser pulse radiation, can be seen;

FIG. 5. illustrates the spectrum of enhanced Raman scattering from thiophenol monolayer, adsorbed on nanostructures, which were formed by an ultrashort pulse laser. Stimulated with 633 nm radiation. Illustrated in the figure: Raman scattering spectrum (12) of thiophenol monolayer, adsorbed on the silver-coated area next to the nanostructured area and the Raman scattering spectrum (13) of the thiophenol monolayer on the nanostructured, silver-coated area of same thickness.

BEST MODE FOR CARRYING OUT THE INVENTION

Detailed Description of Preferred Embodiments

This invention provides a method, where ultra-short laser pulses are used for reducing surface viscosity of a material and interact with the reduced viscosity layer on the material's surface, thus initiating the self-formation of stochastic nanostructures. In the most preferred employment, ultra-short pulse, preferably from 100 fs to 100 ps, laser radiation and an amorphous substrate (1) material are employed.

A solid amorphous material, which has the property of softening under a specific temperature (but not a specific melting point), is called glass. However, the substrate is not limited to being comprised of an entirely amorphous material, but it can also be a crystalline material with amorphous additives or vice versa.

In the most preferred embodiment, the sensor substrate is made of glass, which is mainly composed of silicon dioxide. Such glass can contain alkaline earth metals, and/or other metal, additives, for example silica glass, also called soda-limesilica glass, lead glass, bore-silicate glass, chalcogenide glass, etc. It is important for the sensor production by the method described in this patent, that the substrate material would be amorphous and be characterized by a softening (viscosity decrease) temperature, and not a melting temperature. After exceeding the softening temperature, the glass does not suddenly liquefy, but rather its viscosity starts changing and the specific heat capacity increases. The softening temperature for amorphous materials (glasses) is approximately 1000° C. or less. The lower this temperature is, the lower is the surface (3) damage threshold, meaning that laser pulses of smaller energies are required. However, a material that is softening at lower temperature is less resistant to mechanical impact, furthermore, materials of lower viscosity can be susceptible to the loss of nanostructure shape and such sensors can degenerate—the amplification qualities can decline in time.

SERS sensors are produced by using an ultra-short pulse laser (4) system that additionally can comprise a wavelength conversion (5), optical power (pulse energy) control (6), beam expansion (8) units; for beam delivery, in the most preferred embodiment, mirrors (7) or optical fibers (not shown in figures) are used. While processing the surface, the relative position of the laser beam must be changed with relation to the substrate (1). Usually this is achieved by using galvanometric scanners (9) and/or precision positioning stages (11). In addition, convex lenses or an objective lens (10) comprising a collection of lenses are used for beam focusing.

It should be understood by one skilled in the art that it possible to use other beam shaping methods, which could speed up substrate processing, including splitting of the beam into several beams, the modification of the focused beam crosssection or energy distribution, and others.

The method for producing the SERS sensor comprises the following steps:

I laser beam scanning with respect to the substrate (1);
II washing of the processed substrate (1);
III application of a metal coating;

Short pulse laser textured substrates can be coated with different metal coatings, from which the most suitable are gold, silver, copper, platinum coatings. Also, in some cases aluminum may be used.

In the most preferred embodiment, the laser processed surface area (2) is sputtered or in other ways deposited with a thicker than 100 nm metal coating. In has been noticed, that the thicker the coating is formed, the larger is the enhancement of the sensor. It will be understood by one skilled in the art that any thickness of the metal coating can be employed as long as the island-like surface structure is maintained. A thinner than 100 nm metal coating will also exhibit the enhancement of Raman scattering, however, it will be less intense, as compared to a thicker coating. On the other hand, a too thick coating can diminish the island-like active surface (2) structure and abolish the uncoated gaps between the islands. The properties of such a sensor will be worse. Therefore when choosing the thickness of the metal coating, it is necessary to take note of the texture of the laser treated surface structure.

The metal coating can be applied to the whole surface (3) of the substrate or, by particle deposition through a mask, onto the active surface area (2) only. Yet in another embodiment, the substrate (1) with a plurality of active surface areas (2) is coated with a metal and diced in such a way, that each separate piece of the initial substrate comprises at least one active surface. Later on, the separated sensors can be used directly in Raman scattering measurement systems, or can be glued onto other substrates, for example microscope slides, which are used in microscopy.

The preferred sensor structure is such, that a glass plate, for example a microscope slide or a slip glass is used. One or more active surfaces (2) are formed on the substrate surface. Thereafter, the active surface is covered with a metal coating, most preferably, by using an electron, ion, plasma or magnetron sputtering. In the most preferred embodiment, the active surface is formed in such a way, that it does not extend to the substrate edges. Surface wettability properties differ between the active area (2) and the unprocessed area around it, therefore if the active surface is formed in such a way that its perimeter does not reach the edges of the substrate, it is possible to control the distribution of a liquid analyte better, which has been trickled on the substrate.

Yet in another embodiment, the metal coating process is performed by employing an ultra-short pulse laser. Given a sufficient pulse energy, the same laser, which is used for processing of the sensor surface, can also be used for metal deposition.

Hereinafter an exemplary embodiment of the current invention is disclosed. Following this example, a sensor invention featuring very strong Raman scattering enhancement has been demonstrated. Nonetheless, the disclosed example and the mentioned parameters are provided to help understand the invention better and in no way limit its extent. These parameters can be changed in a wide interval, reproducing similar or different results, yet the main concept of the fabrication process remains the same.

EXAMPLE 1

The surface of a silica glass substrate is processed with femtosecond laser radiation. The duration of a pulse is 300 fs, wavelength 515 nm, and during the irradiation with a single pulse an energy density of 0.032 $J/cm^2$ is achieved on the substrate surface on average. The substrate surface is treated by translating the substrate in such a way that both in the direction of fabrication and in the perpendicular to the translation direction laser pulses overlap by about 70% in the plain of the substrate surface.

During testing of such active surface, an adsorbed monolayer of thiophenol molecules was irradiated with 633 nm wavelength laser radiation; the resultant SERS spectrum is registered and provided in FIG. 5. Herein the silver coating is 100 nm thick. The bottom line (12) represents the enhanced Raman scattering spectrum of the silver surface, present next to the SERS active area (2), and the upper line (13) represents the enhanced Raman scattering spectrum (13) of the analyte, adsorbed to the nanostructures, formed by means of a femtosecond laser. The average optical power of the stimulating laser was 1 mW, and the integration time 100 s.

The invention claimed is:

1. A plasmonic sensor, comprising:
   a substrate,
   a short-pulse laser processed surface area on the substrate, and
   a metal coating deposited on the laser processed surface area on the substrate,
   wherein the substrate comprises an amorphous dielectric material comprising a stochasitic self-organized nanostructure formed of the amorphous dielectric material.

2. The sensor according to claim 1, wherein laser pulses have been overlapped on the laser processed surface of the substrate by translating the substrate with respect to a focused laser beam and an overlap of the laser pulses is in a range of 20% to 80%, both in a direction of translation, and in a perpendicular direction to the translation direction.

3. The sensor according to claim 1, wherein the amorphous dielectric material has a transition temperature, at which a softening of the amorphous dielectric material commences, of less than 1000° C.

4. The sensor according to claim 1, wherein the substrate comprises glass.

5. The sensor according to claim 4, wherein the substrate comprises at least one of lead glass, borosilicate glass, and chalcogenide glass.

6. The sensor according to claim 1, wherein the substrate comprises at least one of a slide and a cover slip.

7. The sensor according to claim 1, wherein the short-pulse laser comprises at least one of a femtosecond laser and a picosecond laser.

8. A method of making a plasmonic sensor, the method comprising:
   processing a dielectric substrate using short laser pulses; and
   applying a metal coating onto a laser processed surface of the dielectric substrate,
   wherein laser pulse duration and pulse energy are selected in such a way, that one or more laser pulses that are incident onto the laser processed surface melt a shallow layer of the dielectric substrate at multiple spots and, under an interaction between the melt and at least one of the laser pulses, stochastic self-organized nanostructures, which are smaller than 1 micrometer, are formed, and wherein the processing comprises irradiating the dielectric substrate with less than 100 laser pulses in each of the multiple spots.

9. The method according to claim 8, wherein the laser pulse duration is in the range from 100 fs to 100 ps.

10. The method according claim 8, wherein the pulse energy is selected in such a way that a laser energy density on a surface of the dielectric substrate is from 100% to 200% of a surface ablation threshold of the dielectric substrate.

11. The method according to claim 10, wherein the laser processed surface of the dielectric substrate receives an average of between about 0.01 and about 0.05 J/cm$^2$ energy density from a single laser pulse.

12. The method according to claim 8, wherein feature size of the stochastic self-organized nanostructures is controlled by at least one of selecting a wavelength of a short pulse laser and by processing the dielectric substrate in a different surrounding medium, and wherein at least one of a shorter wavelength laser radiation and a larger refractive index medium in a processing environment is used for formation of features of a smaller size, and at least one of a longer wavelength laser radiation and a smaller refractive index medium is used for formation of features of a larger size.

13. The method according to claim 8, wherein the metal coating is coated by means of laser-induced sputtering, and wherein deposition of the metal coating is achieved by using radiation of the laser pulse, which is used for the formation of the stochastic self-organized nanostructures on the dielectric substrate.

14. The sensor according to claim 8, wherein less than about 10 laser pulses are used to fabricate each of the multiple spots of the laser processed surface area on the substrate.

15. The method according to claim 9, wherein the dielectric substrate comprises glass.

16. The method according to claim 8, wherein the pulse energy is selected in such a way that a laser energy density on a surface of the dielectric substrate is from 100% to 120% of a surface ablation threshold of the dielectric substrate.

17. The method according to claim 9, wherein feature size of the stochastic self-organized nanostructures is controlled by at least one of selecting a wavelength of a short pulse laser and by processing the dielectric substrate in a different surrounding medium, and wherein at least one of a shorter wavelength laser radiation and a larger refractive index medium in a processing environment is used for formation of features of a smaller size, and at least one of a longer wavelength laser radiation and a smaller refractive index medium is used for formation of features of a larger size.

18. The method according to claim 10, wherein feature size of the stochastic self-organized nanostructures is controlled by at least one of selecting a wavelength of a short pulse laser and by processing the dielectric substrate in a different surrounding medium, and wherein at least one of a shorter wavelength laser radiation and a larger refractive index medium in a processing environment is used for formation of features of a smaller size, and at least one of a longer wavelength laser radiation and a smaller refractive index medium is used for formation of features of a larger size.

19. The method according to claim 9, wherein the metal coating is coated by means of laser-induced sputtering, and wherein deposition of the metal coating is achieved by using radiation of the laser pulses, which is used for the formation of the stochastic self-organized nanostructures on the dielectric substrate.

20. The method according to claim 10, wherein the metal coating is coated by means of laser-induced sputtering, and wherein deposition of the metal coating is achieved by using radiation of the laser pulses, which is used for the formation of the stochastic self-organized nanostructures on the dielectric substrate.

* * * * *